United States Patent [19]

Karrer

[11] Patent Number: 4,725,548

[45] Date of Patent: Feb. 16, 1988

[54] METHOD AND FERMENTER FOR GROWING TISSUE CELLS

[75] Inventor: Daniel Karrer, Wald, Switzerland

[73] Assignee: Chemap AG, Männedorf, Switzerland

[21] Appl. No.: 860,689

[22] Filed: May 2, 1986

Related U.S. Application Data

[63] Continuation of Ser. No. 496,295, May 16, 1983, abandoned.

[30] Foreign Application Priority Data

May 27, 1983 [CH] Switzerland .......................... 3264/82

[51] Int. Cl.[4] .......................... C12N 5/00; C12M 3/00
[52] U.S. Cl. ................... 435/240.1; 435/284; 435/286; 435/311; 435/313
[58] Field of Search .......................... 261/3, 5, 93, 122; 435/311, 313, 284, 287, 288, 299, 286, 240

[56] References Cited

U.S. PATENT DOCUMENTS

| | | | |
|---|---|---|---|
| 3,027,305 | 3/1962 | Freeman | 435/299 |
| 3,801,468 | 4/1974 | Lumb et al. | 435/313 |
| 4,224,413 | 9/1980 | Burbidge | 435/284 |
| 4,289,854 | 9/1981 | Tolbert et al. | 435/286 |
| 4,337,315 | 6/1982 | Fukushima et al. | 435/313 |

OTHER PUBLICATIONS

"Large Scale Cultivation of Animal Cells in Microcarrier Culture" A. L. Wezel and Velden-de Groot, Mar. 1978, Process Biochemistry.

Primary Examiner—James C. Yeung
Assistant Examiner—Noah Kamen
Attorney, Agent, or Firm—Michael J. Striker

[57] ABSTRACT

In submerged growing of tissue cells on microcarriers in a culture medium, the culture medium is alternately aerated or withdrawn from a bottom of a culture container via a sintered plate. An air chamber is formed under the sintered plate.

1 Claim, 3 Drawing Figures

METHOD AND FERMENTER FOR GROWING TISSUE CELLS

This is a continuation of application Ser. No. 496,295, filed May 16, 1983, now abandoned.

BACKGROUND OF THE INVENTION

The present invention relates to a method of and a fermenter for submerged growing of tissue cells on microcarriers.

Growing of tissue cells on carriers, so-called microcarrier-cultures, is known. The carrier on which the tissue cells are grown is composed of very small particles which are maintained in the culture medium in suspension by gentle stirring. The cells grow on the outer surface of this microcarrier in a one-cell layer or monolayer. In accordance with known methods, the microcarrier is sterilized separately in an autoclave or a specially provided carrier, and after this transferred into the fermenter. The aeration during the cultivation is performed as a rule by an aeration ring. The subsequent trypsinization of the culture is carried out in a separate container.

A. L. van Wezel et al., Proc. Biochem. March 1978, starting from page 6, discloses a microcarrier system in which the exchange of the culture medium is performed with the aid of a small sieve filter of high-grade steel with a mesh width of 60μ, which is mounted in the interior of the fermenter. The culture medium is partially drawn and in this fashion is renewed and recirculated. However, the incorporation of this sieve filter into the fermenter hinders the microcarrier during its discharge from the fermenter. In the event of producing human vaccines, the entire culture medium must be withdrawn, and the cells must be purified serum-free.

A so-called perfusion method is also known in which the medium is continuously exchanged by continuously withdrawing a part of the culture medium via a sieve filter and replacing it with new medium. Such a known sieve filter system operates satisfactorily in the case of small quantities and containers. However it possesses the disadvantage that, in the event it is used for treating greater quantities in which the filter surface is incomparably small relative to the liquid to be separated. As a result of this, the fine-mesh fabric clogs very fast, and a purification and subsequent start can be performed as a rule only after its disassembling. The suspension and mounting of the filter is also very difficult, and an additional opening must be provided in the culture container. Big filter must have a wide mounting location in order to not come into contact with the mixer. Any further inserts offer increased requirements to the sterilization because of dead corners which take place in this case. The known methods also do not permit a residual volume separation.

SUMMARY OF THE INVENTION

Accordingly, it is an object of the present invention to provide a method of and an arrangement for submerged growing of tissue cells, which avoids the disadvantages of the prior art.

More particularly, it is an object of the present invention to provide a method of and an arrangement for submerged growing of tissue cells, which make possible separation from the spent substrate and aeration in optimal condition with elimination of the disadvantages of the known methods and fermenters.

In keeping with these objects and with others which will become apparent hereinafter, one feature of the present invention resides, briefly stated, in a method of submerged growing of tissue cells on microcarriers in a culture medium, wherein the culture medium is alternately aerated or withdrawn from a bottom of a culture container.

It is another feature of the present invention that a fermenter for submerged growing of tissue cells is provided with means for alternately aerating or withdrawing a culture medium from a bottom of a culture container, wherein the culture container can be provided in its bottom with a sintered plate.

When the method is performed and the fermenter is designed in accordance with the present invention, the medium accommodated in the fermenter can be aerated and withdrawn or exchanged via the sintered plate at the bottom of the container without losing of cell material or carrier material. The sintered metal plate therefore performs two functions. It is important to provide a sufficient air space under the sintered plate.

The novel features which are considered characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENTS

Figure 1:
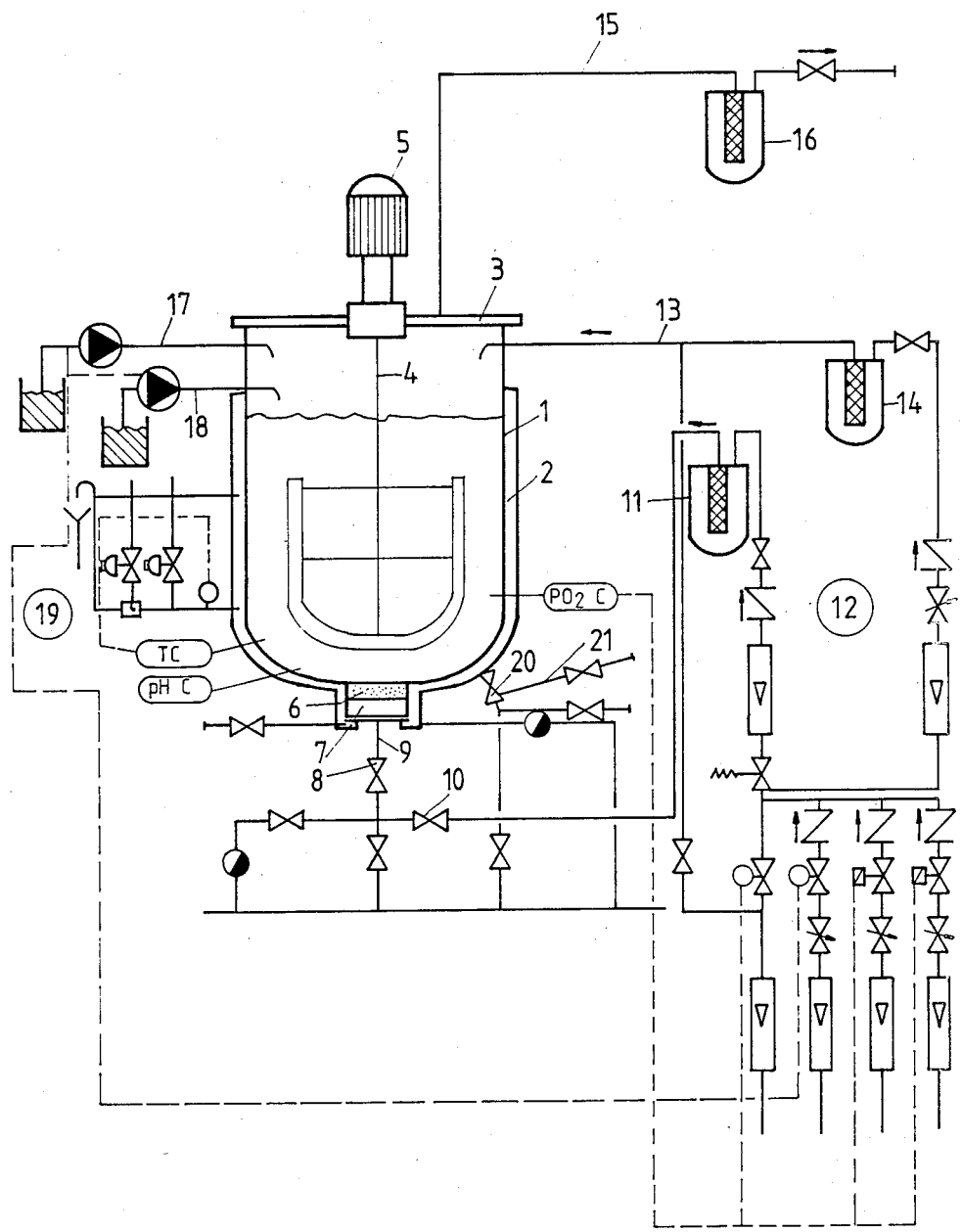
FIG. 1 is a view schematically showing a fermenter for submerged growing of tissue cells, in accordance with the present invention.

A fermenter in accordance with the present invention has a culture container which is identified with reference numeral 1. The culture container is surrounded by a double jacket 2 for maintaining constant the temperature. The culture container 1 has a cover 3 which supports an anchor agitator 4 driven from an electric motor 5.

A sintered plate 6 is arranged in the bottom of the culture container 1, and an air chamber 7 is formed under the sintered plate 6. A valve 8 is connected via a conduit 9 with the air chamber 7 and leads via a further valve 9' and a conduit 10 to a sterile air filter 11. The sterile air filter 11 is supplied from a gas mixing device 12. A conduit 13 leads to the upper part of the culture container for upper surface aeration and is connected with a sterile air filter 14 which, in turn, is connected with the gas mixing or gas sterilizing device 12. A conduit 15 leads from the cover 13 of the culture container 1 to and exhaust filter 16.

Supply conduits 17 and 18 extend from acid or leaching containers for pH correction. The entire fermenter system is provided with measuring and controlling devices. The reference $PO_2C$ means an oxygen control, the reference TC means a temperature control, and the reference pHC means a pH control. A group 19 is provided for the temperature circuit. A harvest valve 20 leads to a harvest pipe 21.

Figure 2:
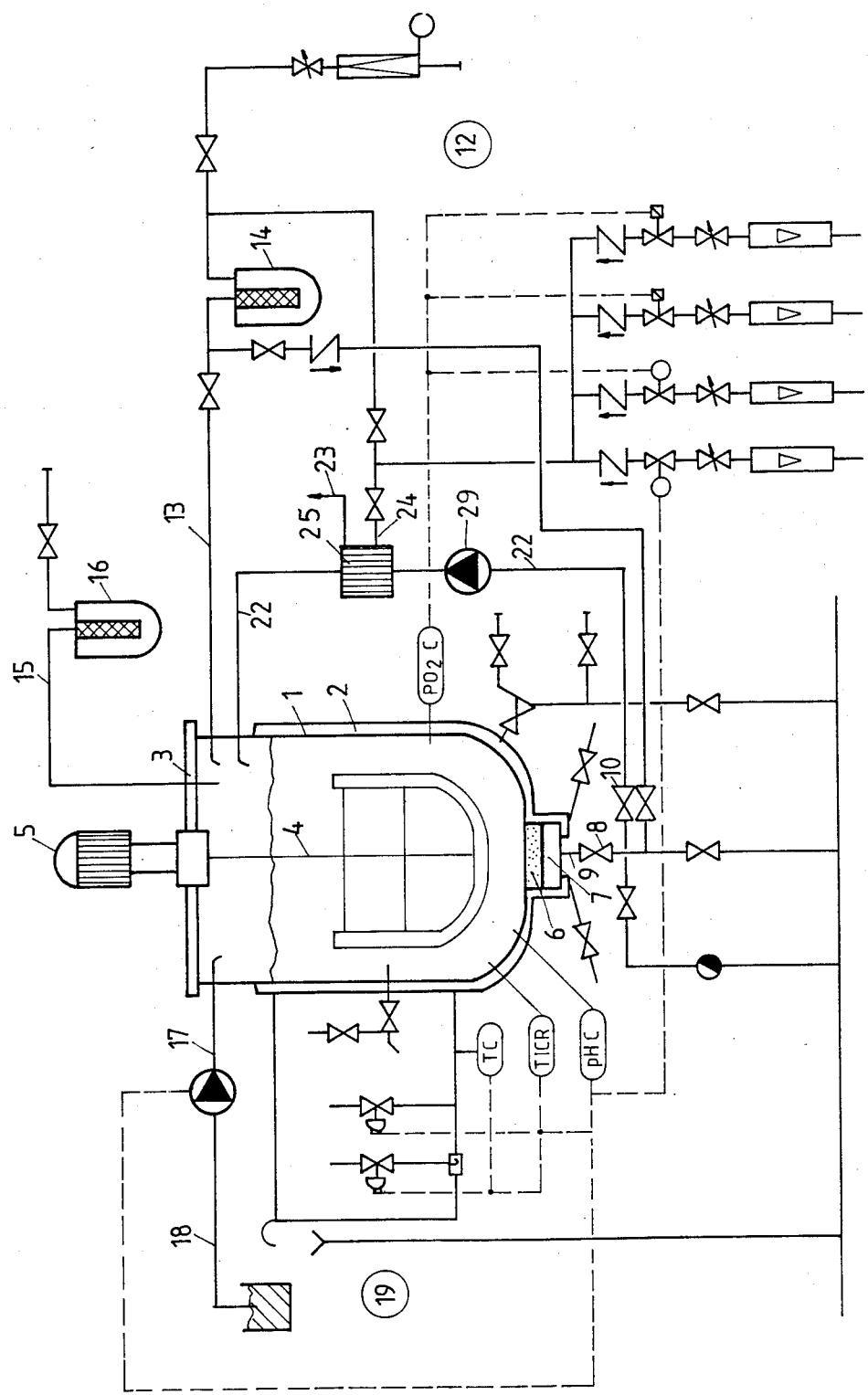
FIG. 2 is a view substantially corresponding to the view of FIG. 1, but showing a fermenter in accordance with a further embodiment of the present invention, including an external permeator.

FIG. 2 shows a fermenter in accordance with a further embodiment of the present invention. In accordance with this embodiment, a permeator 25 is connected in an external circuit via a pump 29 with the culture container 1. A conduit 22 leads back from the permeator 25 into the container 1. A conduct 23 is provided for withdrawal of an excessive gas. A conduit 24 is provided for supply of a gas mixture.

Figure 3:
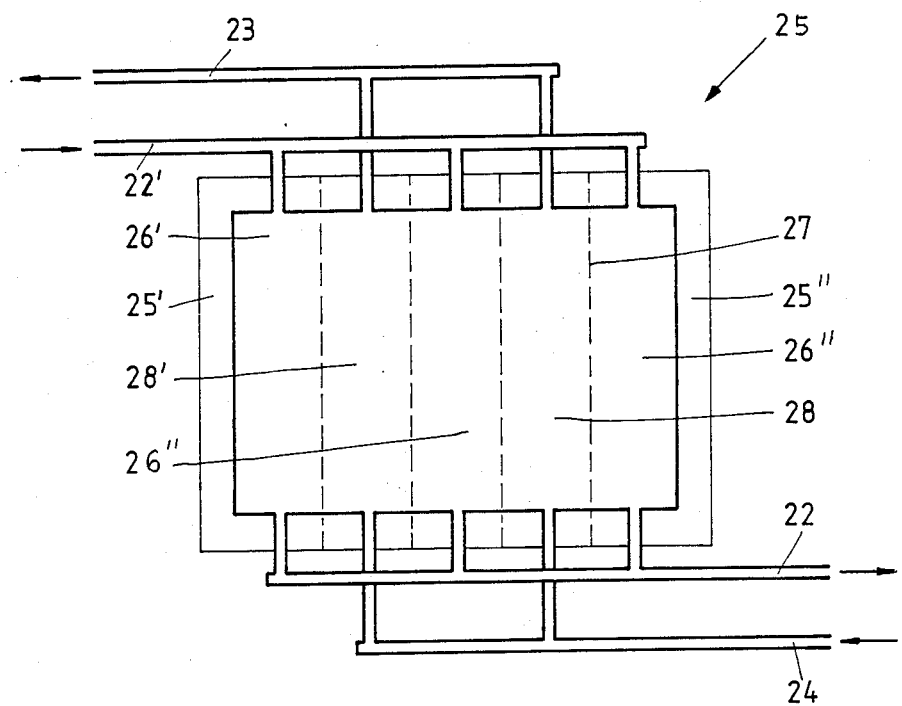
FIG. 3 is a view showing the permeator of FIG. 2 in detail.

As can be seen from FIG. 3, the permeator 25 is formed as a plate permeator. The plate permeator includes a frame composed of a front chamber part 25' and a rear chamber part 25''', and a plurality of chambers 26, 26', 26''' for the medium. The chambers are provided with filtrate channels. Diffusion membranes 27 are arranged on the chambers and composed of a material which is resistant to breaking and coated with silicone. The membranes are coated at their liquid side with silicone, which provides a two-sided gas exchange ($O_2$, $CO_2$) by diffusion.

The permeator 25 is connected with a conduit 22' for supplying the medium, and also with a conduit 22 for withdrawing the medium. A conduit 24 is provided for supplying the gas, and a conduit 23 is provided for withdrawing the gas. Gas chambers 28 and 28' are formed between the chambers 26, 26', and 26''. The gas exchange is carried out by diffusion. The permeator 20 is steam-sterilizable in situ.

During starting the fermenter, the culture container 1 is filled with 10% of its total volume with a buffer solution (PBS Phosphate buffer solution). Also, the microcarrier is supplied and brought to swelling. Then the suspension is sterilized in a known fashion. After this, the PBS is discharged and the culture container is sprayed several times with PBS. Now, sterile-filtrated nutrient medium together with serum is filled to approximately 20% of the total volume. Then the primary culture in form of trypsinized cells is injected, the agitator 4 is slowly rotated during the growing phase, and the residual culture medium is filled. After this, the growing phase is carried out with aeration via the conduit 13 and/or the sintered plate 6. After approximately 48 hours, the aeration is interrupted and the culture medium is discharged via the sintered plate 6. Then the trypsin solution is filled. The trypsinization process is interrupted in a known fashion, and the cells and carrier are transferred via the harvest pipe 21.

In accordance with FIG. 2, the aeration is performed indirectly via a permeate system outside of the culture container proper. The liquid is withdrawn via the sintered plate 6 with both valves 8 and 10 opened, and supplied by the membrane pump 29 through the permeator. Simultaneously, gas is dosed from the gas mixing device 12 via the conduit 22 into the permeator 25. The gasified medium is supplied back via the conduit 22 into the fermenter 1, whereas the exchanged gas is withdrawn via the conduit 23.

The inventive method and arrangement possess a special advantage in the fact that the sterilization and purification of the carrier material are performed in the same container in which the cells are grown. The sintered plate permits a fast medium exchange and provides an exceptional distribution of air which is supplied submerged. The air provides for an additional cleaning effect of the sintered plate. No inserts are necessary inside the culture container. The geometry of the agitator can be freely selected within wide limits. The working volume is varied in the range of between 10 and 80% of the total volume. Also, no transfer of the carrier material, for example for trypsinization of the cells is required. In addition, the medium exchange and conditioning are possible externally.

The external gas exchange via the permeator 20 has an additional advantage. No foam generation takes place in the fermenter 1 in this case. Moreover, shearing forces are reliably prevented by raising air bubbles in the medium. By the selection of thin silicone-coated membranes, a high oxygen transfer takes place with controllable flow. The plate system permits an unobjectionable increase of the permeator by adding of additional plates.

It will be understood that each of the elements described above, or two or more together, may also find a useful application in other types of constructions differing from the types described above.

While the invention has been illustrated and described as embodied in a method of and a fermenter for submerged growing of tissue cells, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of submerged growing of tissue cells on microcarriers in a culture medium, comprising the steps of providing a culture container having a bottom;

filling the culture container with a culture medium and a microcarrier;

providing in the bottom of the container a sintered plate formed so that it allows for aerating the culture medium in the culture container through the sintered plate with simultaneous cleaning of the sintered plate and also allows withdrawing of the culture medium from the container through the sintered plate;

providing culture medium aerating and sintered plate cleaning means, and culture medium withdrawing means outside of the culture container; and alternately connecting the culture aerating and sintered plate cleaning means, and the culture medium withdrawing means with the sintered plate so as to provide alternately aerating the culture medium in the culture container through said sintered plate and clean the sintered plate, and withdrawing the culture medium from the container through the sintered plate.

* * * * *